(12) United States Patent
Noy

(10) Patent No.: US 8,236,855 B2
(45) Date of Patent: Aug. 7, 2012

(54) METHODS OF TREATING METABOLIC DISORDERS

(75) Inventor: Noa Noy, Shaker Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 852 days.

(21) Appl. No.: 12/122,976

(22) Filed: May 19, 2008

(65) Prior Publication Data

US 2009/0137671 A1    May 28, 2009

Related U.S. Application Data

(60) Provisional application No. 60/938,578, filed on May 17, 2007.

(51) Int. Cl.
*A61K 31/22* (2006.01)

(52) U.S. Cl. ...................................... 514/549

(58) Field of Classification Search ............... 514/549, 514/866, 909
See application file for complete search history.

(56) References Cited

FOREIGN PATENT DOCUMENTS

CN         1444932 A   * 10/2003
WO   WO 2005070413 A1 *  8/2005

OTHER PUBLICATIONS

English-translation of CN 1444932A (Oct. 2003).*

* cited by examiner

*Primary Examiner* — Kevin E Weddington
(74) *Attorney, Agent, or Firm* — Tarolli, Sundheim, Covell & Tummino LLP

(57) ABSTRACT

A method of increasing the insulin sensitivity of insulin resistant cells includes administering to the cells an amount of all-trans-retinoic acid effective to activate transcription factor perosixome proliferator-activated receptor (PPAR) β/δ of the cells.

4 Claims, 9 Drawing Sheets

SEQUENCE LISTING

<160> NUMBER OF SEQ ID NOS: 6

<210> SEQ ID NO 1
<211> LENGTH: 21
<212> TYPE: DNA
<213> ORGANISM: Homo sapiens

<400> SEQUENCE: 1
cctctgcttc acaggcaaat a                                           21

<210> SEQ ID NO 2
<211> LENGTH: 24
<212> TYPE: DNA
<213> ORGANISM: Homo sapiens

<400> SEQUENCE: 2
tgcatcagaa gactctcgcc cttt                                        24

<210> SEQ ID NO 3
<211> LENGTH: 24
<212> TYPE: DNA
<213> ORGANISM: Homo sapiens

<400> SEQUENCE: 3
aatcatggaa gccacactgg tggt                                        24

<210> SEQ ID NO 4
<211> LENGTH: 24
<212> TYPE: DNA
<213> ORGANISM: Homo sapiens

<400> SEQUENCE: 4
ccctactttc ctcccatcca gtaa                                        24

<210> SEQ ID NO 5
<211> LENGTH: 24
<212> TYPE: DNA
<213> ORGANISM: Homo sapiens

<400> SEQUENCE: 5
tcacgcctgt aatcccagca cttt                                        24

<210> SEQ ID NO 6
<211> LENGTH: 24
<212> TYPE: DNA
<213> ORGANISM: Homo sapiens

<400> SEQUENCE: 6
tgatttcggc tcactacaac ctcc                                        24

METHODS OF TREATING METABOLIC DISORDERS

RELATED APPLICATION

This application claims priority from U.S. Provisional Application No. 60/938,578, filed May 17, 2007, the subject matter, which is incorporated herein by reference in its entirety.

GOVERNMENT FUNDING

This invention was made with government support under Grant Nos. NIH-CA068150 and NIH-DK060684 awarded by The National Institutes of Health. The United States government has certain rights in the invention.

TECHNICAL FIELD

The present invention generally relates to a method of treating metabolic disorders and more particularly to a method of treating metabolic disorders by administering to insulin resistant cells all-trans-retinoic acid.

BACKGROUND OF THE INVENTION

Metabolic syndrome, also known as syndrome X, is now a global health problem of epidemic proportions. This syndrome denotes a collection of obesity-associated pathologies that include insulin resistance, hyperinsulinemia, enhanced hepatic glucose uptake into the skeletal muscle and fat, elevated levels of circulating free fatty acids, and increased fat accumulation in insulin target tissues. The resulting hyperglycemia, dyslipidemia and hypertension also lead to endothelial dysfunction and thus place metabolic syndrome patients at high risk for atherosclerosis. There is an urgent need for elucidation of the molecular events that result in the development of the metabolic syndrome, and for the identifying novel strategies for prevention and therapy of the disease.

The molecular events that result in the development of the insulin resistance that underlie the metabolic syndrome remain incompletely understood, but available information suggests that the nuclear hormone receptors termed peroxisome proliferator activated receptors (PPARs) play central roles in the process. PPARs are ligand activated transcription factors that appear to function as "lipid-sensors". Like other members of subclass 1 of the superfamily of nuclear hormone receptors, PPAR s interact with the retinoid X receptor (RXR) to form heterodimers that bind to PPAR response elements in regulatory regions of specific target genes. Binding of cognate ligands to these heterodimers result in receptor activation and in upregulation of transcription of the target genes. PPARs thus induce metabolic cascades that upregulate lipid storage, transport, and homeostasis. Three PPAR subtypes, encoded for by three separate genes, are known to exist: PPARα, PPARδ, and PPARγ PPARα is expressed in liver, heart, muscle and kidney, where it regulates fatty acid catabolism. PPARγ is expressed predominantly in adipose tissue and macrophages, where it is involved in adipocyte differentiation, regulation of sugar and lipid homeostasis, and control of inflammatory responses. Thiazolidinediones, synthetic compounds that activate PPARγ are in current use as antidiabetic drugs.

SUMMARY OF THE INVENTION

The present invention relates to a method of increasing the insulin sensitivity of insulin resistant cells. The method includes administering to the insulin resistant cells an amount of all-trans-retinoic acid effective to activate transcription factor perosixome proliferator-activated receptor (PPAR) β/δ of the cells.

In an aspect of the invention, the all-trans-retinoic acid can be administered at an amount effective to induce expression in the cells of at least one of 3-phosphoinositide-dependent protein kinase 1 (PDK-1), fasting induced adipose factor (FIAF) or adipose differentiation-related protein (ADRP). The insulin resistant cells can comprise insulin resistant adipocytes, such as insulin adipocytes cells of an obese subject and/or a subject with metabolic syndrome.

The present invention also relates to a method of treating metabolic syndrome in a mammalian subject. The method includes administering to the subject a pharmaceutical composition comprising all-trans-retinoic acid. The subject can include insulin resistant cells, and the pharmaceutical composition can be administered to the subject in an amount effective to increase the insulin sensitivity of the insulin resistant cells.

In an aspect of the invention, the pharmaceutical composition can be administered at an amount effective to activate transcription factor PPAR β/δ of the insulin resistant cells. The pharmaceutical composition can also be administered at an amount effective to induce expression in the cells of at least one of PDK-1, FIAF, or ADRP. The insulin resistant cells can comprise insulin resistant adipocytes.

The present invention further relates to a method of treating type 2 diabetes caused by insulin resistance of cells in a subject. The method includes administering to the subject an amount of all-trans-retinoic acid effective to increase the insulin sensitivity of the insulin resistant cells. The all-trans-retinoic acid can be administered at an amount effective to activate transcription factor PPAR β/δ of the insulin resistant cells. The all-trans-retinoic acid can also be administered at amount effective to induce expression of at least one of PDK1, FIAF, or ADRP of the insulin resistant cells.

The present invention still further relates to a method of treating obesity or an obesity-related condition in a subject. The method includes administering to the subject an amount of all-trans-retinoic acid effective to increase the insulin sensitivity of insulin resistant cells in the subject. The all-trans-retinoic acid can be administered at an amount effective to activate transcription factor PPAR β/δ of the insulin resistant cells. The pharmaceutical composition can also be administered at amount effective to induce expression in the cells of at least one of PDK-1, FIAF, or ADRP.

In an aspect of the invention the obesity-related condition can be selected from the group consisting of diabetes 2, metabolic syndrome, hyperglycemia, hyperinsulinemia, impaired glucose tolerance, impaired fasting glucose, dyslipidemia, hypertriglyceridemia, insulin resistance, hypercholesterolemia, atherosclerosis, coronary artery disease, peripheral vascular disease, hypertension, and hepatic steatosis.

The present invention still further relates to a method of treating hepatic steatosis in a subject. The method includes administering to the subject an amount of all-trans-retinoic acid effective to reduce hepatic lipid accumulation in the liver. The all-trans-retinoic acid can be administered at an amount effective to activate transcription factor PPAR β/δ of the liver cells. The pharmaceutical composition can also be administered at amount effective to induce expression in the cells of at least one of PDK-1, FIAF, or ADRP.

BRIEF DESCRIPTION OF THE DRAWINGS

The foregoing and other features of the present invention will become apparent to those skilled in the art to which the present invention relates upon reading the following description with reference to the accompanying drawings, in which.

DETAILED DESCRIPTION

Figure 1:
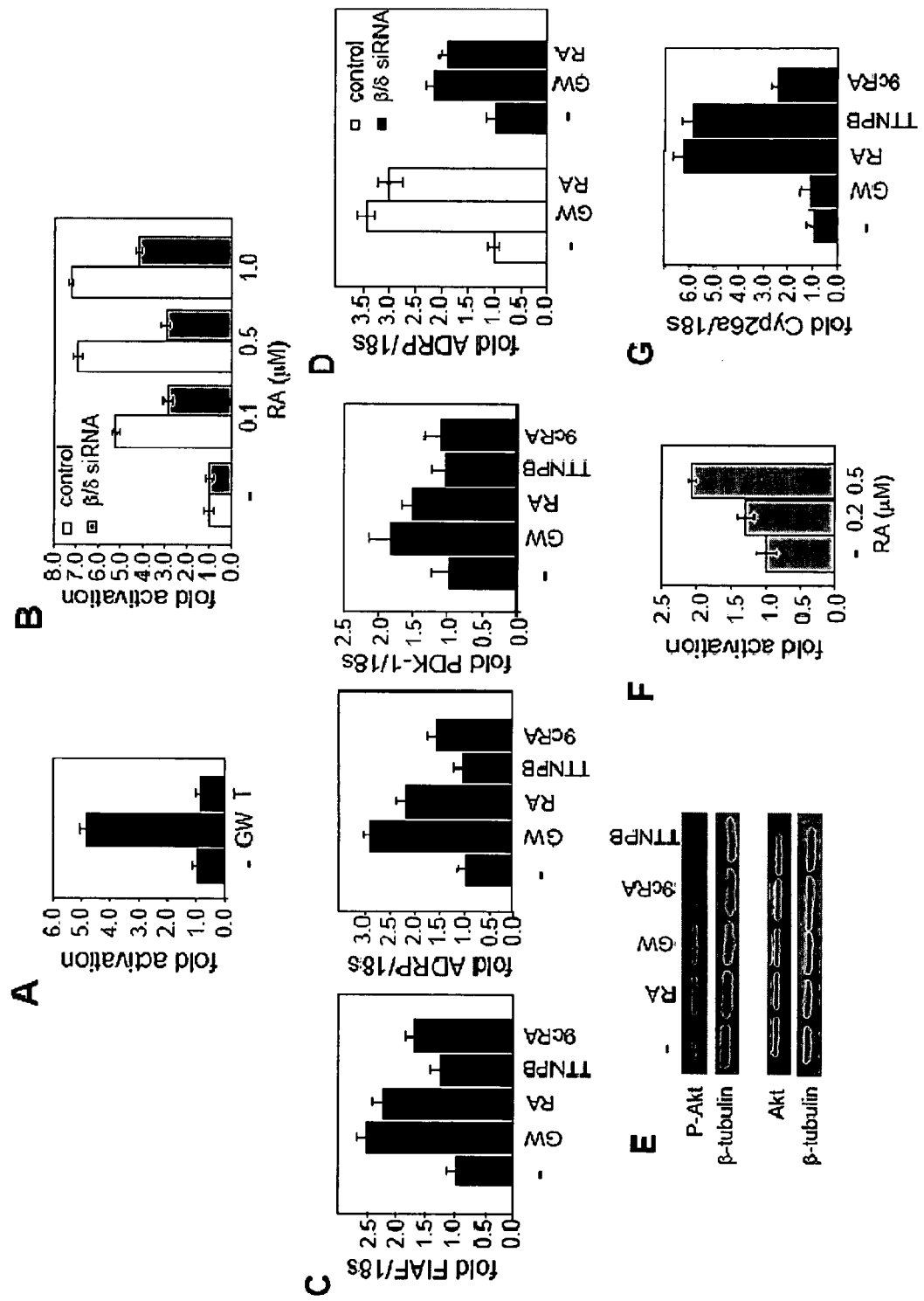
FIG. 1 illustrates: (A) a graph showing the results of the total activation of cells treated with vehicle or GW0742 (GW) or TTNPB (T, 1 μM); (B) a graph showing the results of the total activation of cells cotransfected with either control siRNA or siRNA for PPARβ/δ, and then treated with RA at the denoted concentrations; (C) graphs showing the levels of mRNA of the PPARβ/δ target genes FIAF, ADRP, and PDK-1 expressed from HaCaT cells treated with the denoted ligands (0.1 μM, 4 hr); (D) a graph showing the level of ADRP mRNA in HaCaT cells that were transfected with control siRNA or PPARβ/δ siRNA (24 hr.), and then treated with the denoted ligands (0.1 μM, 4 hr); (E) immunoblots of Thr-307-phospho-Akt, total Akt, and β-tubulin in cells treated with denoted ligands (0.1 μM, 12 hr); (F) a graph of the total activation of HaCaT cells transfected with a RARE-driven luciferase reporter; and (G) a graph of the level of expression of mRNA of the RAR target gene Cyp26a in cells that were treated with the denoted ligands.

It should be understood that the present invention is not limited to particular methods, reagents, compounds, compositions or biological systems, which can, of course, vary. It should also to be understood that the terminology used herein is for the purpose of describing particular aspects of the present invention only, and is not intended to be limiting. Unless defined otherwise, all technical and scientific terms used herein have the same meaning as commonly understood by one of ordinary skill in the art to which the present invention pertains. Although any methods and materials similar or equivalent to those described herein can be used in the practice of the present invention, the preferred materials and methods are described herein. In describing and claiming the present invention, the following terminology will be used.

The term "about" as used herein when referring to a measurable value such as an amount, a temporal duration, and the like, is meant to encompass variations of +20% or ±10%, more preferably ±5%, even more preferably ±1%, and still more preferably ±0.1% from the specified value, as such variations are appropriate to perform the disclosed methods.

The term "therapeutically effective amount" refers to an amount of all-trans-retinoic acid or a derivative thereof that is sufficient to activate the transcription factor peroxisome proliferator-activated receptor δ.

The term "metabolic disorders" refers to a group of identified disorders in which errors of metabolism, imbalances in metabolism, or sub-optimal metabolism occur. The metabolic disorders as described herein also include diseases that can be treated through the modulation of metabolism, although the disease itself may or may not be caused by a specific metabolic defect. Such metabolic disorders may involve, for example, glucose oxidation pathways.

The term "obesity" as used herein is defined in the WHO classifications of weight. Underweight is less than 18.5 BMI (thin); healthy is 18.5-24.9 BMI (normal); grade 1 overweight is 25.0-29.9 BMI (overweight); grade 2 overweight is 30.0-39.0 BMI (obesity); grade 3 overweight is greater than or equal to 40.0 BMI. BMI is body mass index (morbid obesity) and is $kg/m^2$. Waist circumference can also be used to indicate a risk of metabolic complications. Waist circumference can be measured (in cm) at midpoint between the lower border of ribs and the upper border of the pelvis. Other measures of obesity include, but are not limited to, skinfold thickness and bioimpedance, which is based on the principle that lean mass conducts current better than fat mass because it is primarily an electrolyte solution.

The term "obesity-related condition" refers to any disease or condition that is caused by or associated with (e.g., by biochemical or molecular association) obesity or that is caused by or associated with weight gain and/or related biological processes that precede clinical obesity. Examples of obesity-related conditions include, but are not limited to, type 2 diabetes, metabolic syndrome (i.e., Syndrome X), hyperglycemia, hyperinsulinemia, impaired glucose tolerance, impaired fasting glucose, dyslipidemia, hypertriglyceridemia, insulin resistance, hypercholesterolemia, atherosclerosis, coronary artery disease, peripheral vascular disease, hypertension, and hepatic steatosis.

The term "subject" refers to a mammal, such as a human being. As also used herein, the term "subject" may refer to a patient.

The term "pharmaceutical composition" refers to a preparation of one or more of the agents described herein with other chemical components such as physiologically suitable carriers and excipients. The purpose of a pharmaceutical composition is to facilitate administration of an agent to a subject.

The term "insulin resistance" refers to the condition in which normal amounts of insulin are inadequate to produce a normal insulin response from fat, muscle and liver cells. Insulin resistance in fat cells results in hydrolysis of stored triglycerides, which elevates free fatty acids in the blood plasma. Insulin resistance in muscle reduces glucose uptake whereas insulin resistance in liver reduces glucose storage, with both effects serving to elevate blood glucose. High plasma levels of insulin and glucose due to insulin resistance often leads to metabolic syndrome and type 2 diabetes.

The term "metabolic syndrome" refers a combination of medical disorders that increase one's risk for cardiovascular disease and diabetes. It is known under various other names, such as (metabolic) syndrome X, insulin resistance syndrome, Reaven's syndrome. Symptoms and features are fasting hyperglycemia, diabetes mellitus type 2 or impaired fasting glucose, impaired glucose tolerance, or insulin resistance; high blood pressure; central obesity (also known as visceral, male-pattern or apple-shaped adiposity), overweight with fat deposits mainly around the waist; decreased HDL cholesterol; elevated triglycerides; and elevated uric acid levels. Associated diseases and signs are: fatty liver (especially in concurrent obesity), progressing to non-alcoholic fatty liver disease, polycystic ovarian syndrome, hemochromatosis (iron overload); and acanthosis nigricans (a skin condition featuring dark patches).

The present invention generally relates to a method of treating metabolic disorder associated with insulin resistance of cells or tissue of a mammalian subject. The present invention is based on the discovery that all-trans-retinoic acid can activate transcription factor perosixome proliferator-activated receptor (PPAR) β/δ in cells of the subject in which fatty acid binding protein 5 (FABP5) is expressed. Activation of PPAR β/δ in the cells has been shown to induce expression of at least one of 3-phosphoinositide-dependent protein kinase 1 (PDK-1), fasting induced adipose factor (FIAF) or adipose differentiation-related protein (ADRP) in the cells. Expression of PDK-1, FIAF, and ADRP plays a central role in mediating cell responsiveness to insulin and enabling glucose uptake of the cells as well as mediating lipid accumulation in the liver.

Based on these discoveries, the present invention provides methods for treating metabolic disorders associated with insulin resistance, such as obesity, type 2 diabetes, metabolic syndrome, and other obesity related conditions.

One aspect of the invention therefore relates to a method increasing insulin sensitivity in insulin resistant cells of a subject being treated. The method includes administering to the insulin resistant cells an amount of all-trans-retinoic acid effective to activate transcription factor perosixome proliferator-activated receptor (PPAR) β/δ of the cells.

The all-trans-retinoic acid administered to subject has the following general formula:

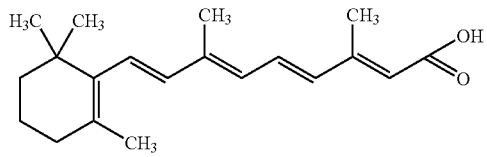

The all-trans-retinoic acid is commercially available from, for example, Sigma Chemical (St. Louis, Mo.) and BASF Pharma Solutions. The all-trans-retinoic acid can also be synthesized as described, for example, in U.S. Pat. No. 5,808,120, which is herein incorporated by reference in its entirety.

The all-trans-retinoic acid can be administered to the subject in an amount effective to induce expression of at least one of 3-phosphoinositide-dependent protein kinase 1 (PDK-1), fasting induced adipose factor (FIAF) or adipose differentiation-related protein (ADRP) in the insulin resistant cells. In one aspect of the invention, the insulin resistant cells can comprise insulin resistant adipocytes of an obese subject, a subject with a metabolic disorder, and/or a subject with metaboic syndrome. All-trans-retinoic acid administered to adipocytes of the subject can activate PPAR δ in adipocytes, thereby inducing expression of at least one of PDK1, FIAF, or ADRP. Upregulated expression of PDK-1 can sensitizes the insulin resistant cell to insulin activity enabling glucose activity and the treatment of various metabolic disorders. Upregulated expression of FIAF and/or ADRP can lower lipid accumulation and fat accumulation in the subject.

The various metabolic disorders associated with insulin resistance that can be treated with the all-trans-retinoic acid include, for example, obesity and obesity related conditions (e.g., type 2 diabetes, atherosclerosis), and metabolic syndrome. It will be appreciated that other metabolic disorders associated with insulin resistance can be treated with the all-trans-retinoic acid in accordance with the present invention.

The all-trans-retinoic may be administered to a subject by any conventional route of administration, including, but not limited to, intravenous, oral, subcutaneous, intramuscular, intradermal and parenteral administration. Preferably, formulations are for parenteral (e.g., intravenous) or oral administration.

The all-trans-retinoic acid can be provided in a pharmaceutical composition for administration to the subject. The dosage of the composition including all-trans-retinoic acid administered to the subject may be varied over a wide range from 1 to 1000 mg per adult human per day. For oral administration, the compositions are preferably provided in the form of tablets containing, for example, about 0.01, 0.05, 0.1, 0.5, 1.0, 2.5, 5.0, 10.0, 15.0, 25.0, 50.0, 100, 150, 200, 250 or 500 milligrams of the all-trans-retinoic acid for the symptomatic adjustment of the dosage to the patient to be treated. The all-trans-retinoic acid may be administered, for example, on a regimen of 1 to 2 times per day. The dosages, however, may be varied depending upon the requirement of the patients, the severity of the condition being treated and the compound being employed. The use of either daily administration or post-periodic dosing may be employed.

The compositions can be provided in unit dosage forms such as tablets, pills, capsules, powders, granules, sterile parenteral solutions or suspensions, metered aerosol or liquid sprays, drops, ampoules, auto-injector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection.

For preparing solid compositions, such as tablets, the all-trans-retinoic acid can be mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid homogenous preformulation composition.

When referring to these preformulation compositions as homogeneous, it is meant that the active ingredient or ingredients are dispersed evenly throughout the composition so that the composition may be readily subdivided into equally effective dosage forms such as tablets, pills and capsules. This solid preformulation composition is then subdivided into unit dosage forms of the type described above containing from 0.1 to about 500 mg of all-trans-retinoic acid.

The tablets or pills of the composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer, which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the pharmaceutical compositions including all-trans-retinoic acid may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Examples of dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin. The liquid forms in suitably flavored suspending or dispersing agents may also include the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

Advantageously, pharmaceutical compositions including all-trans-retinoic acid may be administered in a single daily dose, or the total daily dosage may be administered in divided doses of two, three or four times daily. Furthermore, pharmaceutical compositions including all-trans-retinoic acid can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the all-trans-retinoic acid can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

Optimal dosages to be administered may be readily determined by those skilled in the art, and will vary with the particular compound used, the strength of the preparation, the mode of administration, and the advancement of the disease condition. In addition, factors associated with the particular patient being treated, including patient age, weight, diet and time of administration, will result in the need to adjust dosages.

The all-trans-retinoic pharmaceutical compositions of the present invention can also be administered in the form of liposome delivery systems, such as small unilamellar vesicles, large unilamellar vesicles, and multilamellar vesicles. Liposomes can be formed from a variety of lipids, including but not limited to amphipathic lipids such as phosphatidylcholines, sphingomyelins, phosphatidylethanolamines, phophatidylcholines, cardiolipins, phosphatidylserines, phosphatidylglycerols, phosphatidic acids, phosphatidylinositols, diacyl trimethylammonium propanes, diacyl dimethylammonium propanes, and stearylamine, neutral lipids such as triglycerides, and combinations thereof. They may either contain cholesterol or may be cholesterol-free.

EXAMPLES

Example 1

In HaCaT Keratinocytes, RA Activates PPARβ/δ in Parallel to Activation of RAR

The ability of RA to activate PPARβ/δ in the human keratinocyte cell line HaCaT was examined. Transactivation assays were conducted in HaCaT cells transfected with a PPRE-driven luciferase reporter. Cells were treated with the ligands denoted in FIG. 1 for 15 hours, lysed and luciferase activity was measured and corrected for β-galactosidase activity. Data was normalized to the basal activity. Data are mean±SEM, n=3

FIG. 1A illustrates a graph showing the results of the total activation of cells treated with vehicle or GW0742 (GW) or TTNPB (T, 1 µM). FIG. 1B illustrates a graph showing the results of the total activation of cells cotransfected with either control siRNA or siRNA for PPARβ/δ, and then treated with RA at the denoted concentrations. FIG. 1C illustrates graphs showing the levels of mRNA of the PPARβ/δ target genes FIAF, ADRP, and PDK-1 expressed from HaCaT cells treated with the denoted ligands (0.1 µM, 4 hr). Levels of mRNA of the PPARβ/δ target genes FIAF, ADRP, and PDK-1 were analyzed by Q-PCR and normalized to 18s mRNA. FIG. 1D illustrate a graph showing the level of ADRP mRNA in HaCaT cells that were transfected with control siRNA or PPARβ/δ siRNA (24 hr.), and then treated with the denoted ligands (0.1 µM, 4 hr). ADRP mRNA was analyzed by QPCR and normalized to 18s mRNA. Data are mean±SEM, n=3. FIG. 1E illustrates immunoblots of Thr-307-phospho-Akt, total Akt, and β-tubulin in cells treated with denoted ligands (0.1 µM, 12 hr). Data from a representative experiment, which was repeated 4 times with similar results are shown. FIG. 1F illustrates a graph of the total activation of HaCaT cells transfected with a RARE-driven luciferase reporter. Cells were treated with RA at the denoted concentrations (15 hr), lysed, and luciferase activity measured and corrected for β-galactosidase activity. Data were normalized to the basal activity. *Data are mean±SEM, n=3*. FIG. 1G illustrates a graph of the level of expression of mRNA of the RAR target gene Cyp26a in cells that were treated with the denoted ligands. Expression of mRNA of the RAR target gene Cyp26a was analyzed by Q-PCR and normalized to 18s mRNA. Data are mean±SEM, n=3.

Transcriptional activation assays showed that the synthetic PPARβ/δ-selective ligand GW0742, but not the RAR-selective ligand 4-[(E)-2-(5,6,7,8-Tetrahydro-5,5,8,8-tetramethyl-2-naphthalenyl)-1-propenyl]benzoic acid (TTNPB), induced transcription of the reporter (FIG. 1A). These observations attest to the expression and functionality of PPARβ/δ in these cells and demonstrate specificity of reporter response. RA also enhanced the expression of the PPRE-driven reporter and did so in a dose responsive manner (FIG. 1B). The response was markedly suppressed when the expression of PPARβ/δ in the cells was decreased by about 80% by siRNA methodology (FIG. 1B), indicating that the ability of RA to induce reporter expression was indeed mediated by this receptor and not by RAR.

We then set out to examine the ability of RA to induce the expression of endogenous PPARβ/δ target genes in HaCaT cells. One of these, PDK-1, is a direct PPARβ/δ target in HaCaT cells. Two other genes, fasting induced adipose factor (FIAF) and adipose differentiation-related protein (ADRP), are targeted by PPARβ/δ in other cells.

Figure 3:
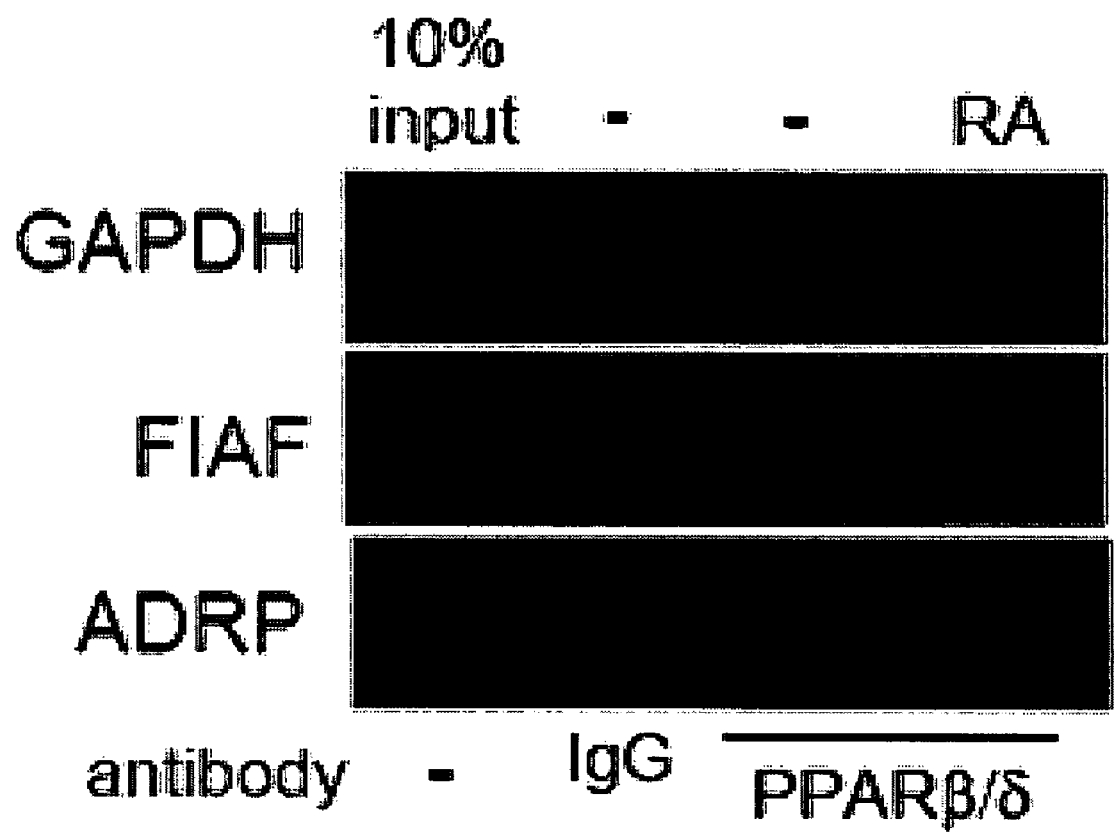
FIG. 3 illustrates immunoblots showing PPAR β/δ associates with the PPRE of the ADRP and FIAF genes in live-HaCaT cells.

FIG. 3 illustrates PPAR β/δ associates with the PPRE of the ADRP and FIAF genes in live HaCaT cells, verifying that both are direct targets for this receptor in the context of these cells. Chromatin immunoprecipitation assays were conducted in HaCaT cells using pre-immune IgG or antibodies against PPARβ/δ. The regions containing the PPRE of the ADRP and FIAF genes were amplified using appropriate primers. A 220 bp region 6-kb upstream from the strat site of GAPDH was used as a negative control.

The PPARβ/δ ligand GW0742 as well as RA upregulated the expression of mRNA for all three of these endogenous PPARβ/δ target genes (FIG. 1C). The observations that the RAR-ligand TTNPB had little effect on the expression of these genes further confirm that RAR is not involved in this activity of RA. As a control, cells were treated with 9-cis-RA (9cRA), a ligand that activates RXR, the obligatory heterodimerization partner for both RAR and PPARs. This ligand induced a modest response, which likely emanated from activation of the RXR moiety of the RXR-PPARβ/δ heterodimer. The small magnitude of the response indicates that the induction of ADRP and FIAF by RA is not a result of conversion of RA to its 9-cis isomer within the cells. Further support for the conclusion that upregulation of these genes by RA is mediated by PPARβ/δ was provided by the observations that an 80% decrease in the expression of this receptor significantly hampered the induction of ADRP by both GW0747 and RA (FIG. 1D).

Notably, one of the PPARβ/δ targets found to be induced by RA, PDK-1, is an important component of the anti-apoptotic activities of this receptor in keratinocytes, where induction of this kinase leads to phosphorylation and activation of the downstream PDK-1-target survival factor Akt. The effects of RA or GW0742 on the phosphorylation level of Akt were thus examined. Treatment with either of these ligands, but not with TTNPB or 9cRA, significantly increased the phosphorylation level of Akt (FIG. 1E).

In addition to activating PPARβ/δ, RA also upregulated the expression of a reporter gene construct driven by an RAR response element (FIG. 1F), and it efficiently upregulated the expression of mRNA for CYP26a, a known direct RAR target gene (FIG. 1G). Hence, in HaCaT cells, RA treatment results in parallel activation of both RAR and PPARβ/δ.

FABP5 Translocates Into the Nucleus in Response to RA, and it Enhances RA Induced, PPARβ/δ-Mediated Transcriptional Activation.

The observations that RA can activate both RAR and PPARβ/δ raise the question of the factors that regulate the dual activity of this hormone. The iLBPs CRABP-II and FABP5 mobilize to the nucleus in response to ligands that activate RAR and PPARβ/δ, respectively, and they bind to their cognate receptors to form a complex through which the ligand is directly 'channeled' to the receptor. Consequently, CRABP-II enhances the transcriptional activity of RAR, while FABP5 facilitates the activation of PPARβ/δ. The observations that RA serves as a ligand for PPAR β/δ thus raise the possibility that RA may be delivered to this receptor by FABP5.

Figure 2:
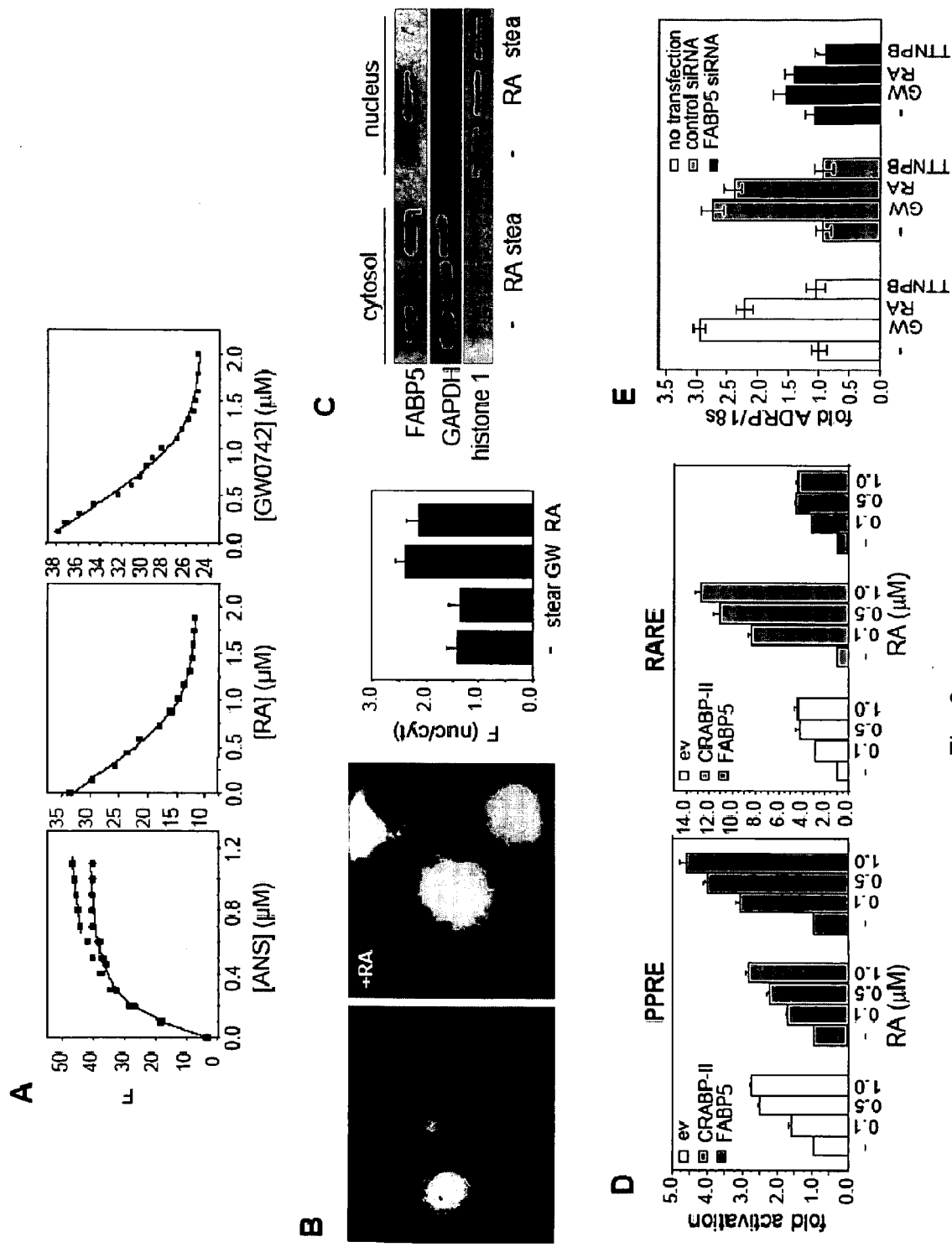
FIG. 2 illustrates: (A) titration curves of fluorescence of FABP5 titrated with the fluorescence probe ANS; (B) images of COS-7 cells transfected with an expression vector harboring GFP-FABP5; (C) an immunoblot of HaCaT cells treated with denoted RA or with stearic acid (1 μM, 30 min.); (D) graphs of the results of transactivation assays carried out in COS-7 cells cotransfected with a luciferase reporter driven by a PPRE and an expression vector for PPARβ/δ (left panel) or with an RARE-driven reporter together with an expression vector for RARα (right panel); and (E) a graph of the results of HaCaT cells not transfected, or transfected with either control siRNA or a construct harboring FABP5 siRNA (24 hr.).

FIG. 2A illustrates titration curves of fluorescence of FABP5 titrated with the fluorescence probe ANS. Titrations curves (left panel, filled squares) were corrected for linear non-specific fluorescence (solid line at end of titration curve), and corrected data (filled circles) analyzed to yield a Kd of 57±7.3 nM (mean±SD, n=3). Kds for the association of FABP5 with RA (middle panel) and with GW0742 (right panel) were determined by fluorescence competition titrations. FIG. 2B illustrates images of COS-7 cells transfected with an expression vector harboring GFP-FABP5. Images were acquired from live cells before and after a 30 min. treatment with RA (1 µM). Right panel: quantitation of nuclear/cytoplsmic partitioning of FABP5 in cells treated with denoted ligands. Forty cells of each treatment group were analyzed (mean±SEM). FIG. 2C illustrates an immunoblot of HaCaT cells treated with denoted RA or with stearic acid (1 µM, 30 min.). Nuclei were separated from cytosol by subcellular fractionation (Calbiochem ProtoExtract Subcellular Proteome Extraction kit) and analyzed for the presence of FABP5 by immunoblots. FIG. 2D illustrates graphs of the results of Transactivation assays carried out in COS-7 cells cotransfected with a luciferase reporter driven by a PPRE and an expression vector for PPARβ/δ (left panel) or with an RARE-driven reporter together with an expression vector for RARα (right panel). Cells were also transfected with an empty vector or with expression vectors for either FABP5 or CRABP-II, treated with RA, lysed, and luciferase activity determined. Data are mean±SEM, n=3. FIG. 2E illustrates a graph of the results of HaCaT cells not transfected, or transfected with either control siRNA or a construct harboring FABP5 siRNA (24 hr.). The ability of denoted ligands to induce ADRP expression was monitored by Q-PCR and normalized to 18s mRNA. Data are mean±SEM, n=3.

The fluorescence-based binding assay (FIG. 2A) demonstrated that GW0742 and RA bind to FABP5 with Kds of 42.3±4.5 nM, and 34.8±6.6 nM, respectively (mean±SD, n=3), in good agreement with binding affinities of this protein towards other ligands. The subcellular localization of FABP5 was then examined. COS-7 cells were transfected with FABP5 fused to green fluorescence protein (GFP), and confocal fluorescence microscopy was used to image GFP-FABP5 in live cells treated with various ligands (FIG. 2B). Similarly to the behavior of GFP when transfected alone, GFP-FABP5 in untreated cells distributed between the cytoplasm and the nucleus, most likely reflecting that over-expression of the protein leads to leakage into the nucleus even in the absence of a specific nuclear localization signal (data not shown). Treatment of cells with stearic acid, a long chain fatty acid that binds FABP5 but does not activate it, did not affect the subcellular distribution of the protein. In contrast, treatment with either GW0742 or RA resulted in a distinct shift of the protein into the nucleus (FIG. 2B). To monitor the effects of ligands on the localization of endogenous FABP5 in HaCaT cells, cells were treated with vehicle, RA, or stearate, subjected to subcellular fractionation, and the presence of FABP5 in cytosol and in nuclei examined by immunoblots (FIG. 2C). The data demonstrated that endogenous FABP5 in HaCaT cells is predominantly cytosolic in the absence of ligand, and that it accumulates in the nucleus in response to RA, but not upon treatment with stearic acid. Hence, like known PPAR β/δ-ligands, RA activates the nuclear localization of FABP5.

The effects of FABP5 on the ability of RA to activate PPAR β/δ were examined by transactivation assay using COS-7 cells, which express very low level of either FABP5 or CRABP-II. Cells were co-transfected with a luciferase reporter construct driven by a PPRE, an expression vector for PPARβ/δ, and a vector harboring cDNA for either FABP5 or CRABP-II. Cells were then treated with RA, and the expression of the reporter monitored (FIG. 2D, left panel). RA enhanced the expression of the PPRE-driven reporter in a dose-responsive manner. While expression of CRABP-II did not affect the activity, FABP5 significantly enhanced RA-induced, PPARβ/δ-mediated transactivation. To investigate the effect of the binding proteins on RA-induced activation of RAR, cells were transfected with a luciferase reporter under the control of an RAR response element (RARE), an expression construct for RARα, and a vector harboring cDNA for either FABP5 or CRABP-II. In agreement with previous reports, CRABP-II augmented RAinduced transactivation of RAR. On the other hand, FABP5 had little effect on this activity (FIG. 2D, right panel). Cells in which the receptors were not ectopically expressed displayed qualitatively similar behaviour but the magnitudes of the ligand-induced responses were significantly smaller (not shown).

The involvement of FABP5 in RA-induced activation of PPARβ/δ was further investigated by examining the effect of decreasing the expression level of this binding protein on the ability of RA to activate the receptor in HaCaT cells. Cells were transfected with FABP5 siRNA, resulting in an about 80% decrease in the level of the protein, and induction of the PPARβ/δ target gene ADRP was monitored (FIG. 2E). Decreasing the expression of FABP5 markedly attenuated the ability of both GW0742 and RA to upregulate the expression of the ADRP, further substantiating that the presence of FABP5 is necessary for efficient activation of PPARβ/δ by its ligands, including RA.

The present work demonstrates that RA serves as a physiological ligand for PPARP/6 under some but not all circumstances. However, this receptor displays near ubiquitous tissue expression, raising the question of the nature of the ligand(s) that activate it in tissues that do not support activation by RA. The ligand binding pocket of PPARβ/δ is much larger than the pockets of other nuclear receptors. It may thus accommodate multiple ligands, and it has been suggested that various long chain fatty acids and eicosanoids may serve as effective PPARβ/δ activators. Whether some of these ligands function as true physiological ligands for the receptor remains to be clarified, but the present work and the similar nature of ligands that bind to FABPs and PPARs raise the possibility that FABPs other than FABP5 may act to deliver ligands other than RA to PPARβ/δ, and thus that they may regulate the functionality of distinct ligands in specific tissues.

When enabled, RA signalling through PPARβ/δ has profound functional consequences. One consequence, explored here, is that such signalling evokes potent anti-apoptotic activities that overcome the growth-inhibitory activities of RAR, and allow cells to survive in the face of powerful apoptotic agents. Hence, RA-dependent maintenance of skin integrity, proliferation of basal keratinocytes, and survival of these cells during wound repair likely stem from a high expression level of FABP5, enabling RA to activate PPARP/6.

Experimental Procedures

Reagents CRABP-II antibodies were provided by Pierre Chambon (IGMCB, Strasbourg, France). FABP5 antibodies were purchased from BioVender (Candler, N.C.). Antibodies against full-length and cleaved PARP, and total and phospho-Akt (Thr308) were from Cell Signaling Technology. Anti-mouse and anti-rabbit immunoglobulin antibodies conjugated to horseradish peroxidase were from Amersham (Arlington Heights, Ill.) and BioRad (Hercules, Calif.), respectively. Anilinonaphtalene-8-sulphonic acid (ANS), RA, TNFα, and TRAIL were from Sigma Chemical Co. (St. Louis, Mo.). 4-[(E)-2-(5,6,7,8-Tetrahydro-5,5,8,8-tetramethyl-2-naphthalenyl)-1-propenyl]benzoic Acid (TTNPB) and GW0742 were purchased from Biomol International (Plymouth Meeting, Pa.) and Toronto Research Diagnostics Inc. (Toronto, ON), respectively.

Proteins. Histidine-tagged CRABP-II and GST-tagged FABP5 were expressed in the *E. coli* strain BL21. Bacteria were grown overnight at 25° C. and protein expression was induced with 0.5 mM isopropyl-β-D-thiogalactopyranoside (IPTG) overnight. Bacteria were pelleted and lysed in lysis buffer (20 mM Tris, pH 8.0, 0.5 mM NaCl, 100 µM phenyl-methylsulfonyl fluoride) containing lysozyme and DNAse I. Mixtures were incubated (30 min., 37° C.), centrifuged, and proteins purified by affinity chromatography, and dialyzed against lysis buffer.

Cells. COS-7, HaCaT, NaF, and MCF-7 cells were maintained in Dulbecco's modified Eagle's medium (DMEM) supplemented with 10% charcoal-treated newborn bovine calf serum (Cocalico Biologicals Inc., Reamstown, Pa.). COS-7 cells were transfected using Fugene (Roche Diagnostics Corporation). Other cell lines were transfected using Superfect (Qiagen).

Transactivation assays. Cells were cultured in 24-well plates and co-transfected with $(PPRE)_3$-luciferase reporter vector (100 ng), a vector harboring the appropriate iLBP (in pCDNA 3.1, 200 ng), and pCH110, a β-galactosidase expression plasmid (50 ng). In some experiments, an expression vector encoding RAR or PPARβ/δ (in pSG5, 50 ng) was cotransfected. Transfections were carried out using Fugene (Roche Diagnostics Corporation) according to the protocol of the manufacturer. Twenty-four hours following transfection, medium was replaced by DMEM, and ligands were added (RA—in ethanol, other ligands—in dimethylsulfoxide). Following 24 hr of treatment, cells were lysed and lysates assayed for luciferase activity (Luciferase assay system, Promega) which was corrected for β-galactosidase activity. Experiments were carried out in triplicates.

Apoptosis was evaluated using the APOPercentage Apoptosis Assay kit (Biocolor Ltd. United Kingdom). $1\times10^6$ cells were suspended in 1 ml medium and dispensed into 96-well microplates. Cells were grown overnight, treated with appropriate ligand (2 hr.) and apoptosis induced with TNFα or TRAIL overnight. Medium was replaced with medium containing APOPercentage Dye Label. The APOP % Dye Release Reagent was added and a microplate colorimeter was used to measure cell-bound dye recovered in solution. Apoptotic index was measured at λ-595 nm.

Binding assays were carried out by fluorescence titrations using a Fluorolog 2 DMIB spectrofluorometer (SPEX Instruments, Edison, N.J.). FABP5 was bacterially expressed and purified and the equilibrium dissociation constants (Kd) that characterize its interactions with RA and GW0742 were measured by fluorescence competition assays. The method entails two steps (Lin et al., 1999). In the first step, Kd for the association of the protein with the fluorescent fatty acid probe ANS was measured. Protein (1 µM) was titrated with ANS from a concentrated solution in ethanol. Ligand binding was monitored by following the increase in the fluorescence of the ligand upon binding to the protein ($\lambda_{ex}$-370 nm; $\lambda_{em}$-475 nm). Titration curves were analyzed (Norris and Li, 1998) to yield the number of binding sites and Kd. Kds for binding of non-fluorescent ligands were then measured by monitoring their ability to compete with fluorescent probes for binding. The protein was pre-complexed with ANS at 1:1 molar ratio and titrated with RA or GW0742 whose binding was reflected by a decrease in probe fluorescence. Kds were extracted from the EC50 of the competition curve and the measured Kd for the probe. Analyses were carried out using Origin 7.5 software (MicroCal Software Inc., Northampton, Mass.).

Quantitative real-time PCR (Q-PCR). RNA was extracted and cDNA generated using Gene Amp RNA PCR (Applied Biosystems, Foster City, Calif.). Q-PCR analyses for PDK-1 were conducted using TaqMan chemistry and Assays on Demand probes (Applied Biosystems, PDK1-Hs00176884_m1, ADRP-Hs00765634_m1, FIAF-Hs00211522_m1), Cyp26a-Hs00175671-g1, BTG2-Hs00198887_m1, cyclin D1 0 Hs00277039-m1. 18S ribosomal RNA (4319413E-0312010) was used as a loading control. Analyses were carried out using the relative standard curve method (Applied Biosystems Technical Bulletin no. 2).

Confocal fluorescence microscopy. COS-7 cells were plated in 35 mm glass bottom microwell dishes (Mattek) in DMEM containing 5% charcoal-treated FBS (75,000 cells per plate), grown for 12 hr. and transfected using Fugene (Roche) with an expression vector harboring GFP-tagged FABP5 (EGFP, 250 ng DNA per plate). Following a 48 hr incubation, medium was replaced with serum-free DMEM, and live cells were imaged using a Leica TCS SP2 confocal microscope equipped with a 40× oil immersion lens. After imaging, cells were treated with ligands (1 µM), incubated at 37° C. for 30 min and imaged again. An average of 40 cells were analyzed using ImageJ (National Institute of Health).

Chromatin immunoprecipitation assays. Nearly confluent HaCat cells were treated with vehicle or RA (1 µM, 45 min.). Proteins were cross-linked to DNA (1% formaldehyde, 10 min.). Cells were washed with PBS, scraped, collected, lysed (1% SDS, 10 mM EDTA, 50 mM Tris, pH 7.9, 1 mM DTT, and protease inhibitors (Roche), and incubated on ice (45 min.). Samples were sonicated three times, and chromatin precleared with protein A beads (2 hr.). Antibodies against PPARβ/δ (H-74, Santa Cruz) or pre-immune rabbit IgG were added and mixtures incubated overnight at 4° C. Protein A beads were added and mixed (2 hr., 4° C.). Beads were washed twice with low-salt buffer (150 mM NaCl, 0.5% deoxycholate, 0.1% Nonidet P-40, 1 mM EDTA, 50 mM Tris-HCl), twice with high salt buffer (low salt buffer+500 mM NaCl), and twice with Tris-EDTA buffer. Cross-link was then reversed (100 mM NaHCO$_3$, 1% SDS, overnight 65° C.), proteins digested with proteinase K (1 hr.), and DNA purified (nucleotide extraction kit, Qiagen). The PPRE containing regions of ADRP and FIAF were amplified by PCR using the following primers. ADRP: 5'-CCTCTGCTTCACAG-GCAAATA-3' (forward) (SEQ ID NO: 1) and 5'-TGCATCA-GAAGACTCTCGCCCTTT-3' (reverse) (SEQ ID NO: 2); FIAF: 5'-AATCATGGAAGCCACACTGGTGGT-3' (forward) (SEQ ID NO: 3) and 5'-CCCTACTTTCCTCCCATC-CAGTAA-3' (reverse) (SEQ ID NO: 4). Primers specific for a region 6-kb upstream of the GAPDH promoter, 5'-TCACGC-CTGTAATCCCAGCACTTT-3' (forward) (SEQ ID NO: 5) and, 5'-TGATTTCGGCTCACTACAACCTCC-3' (reverse) (SEQ ID NO: 6), were used as a negative control.

Example 2

One part of our concept is that retinoic acid sensitizes cells to insulin action, and that it does so by activating the transcription factor PPAR β/δ

To test this hypothesis, we treated cultured adipocytes with: 1) GW0742, a synthetic ligand for PPAR β/δ; 2) TTNPB, a synthetic ligand for the classical retinoic acid receptor (RAR); and 3) retinoic acid. We then used real-time PCR to examine the effects of these ligands on the expression of PDK1 and another known PPAR β/δ target gene, FIAF.

Figure 4:
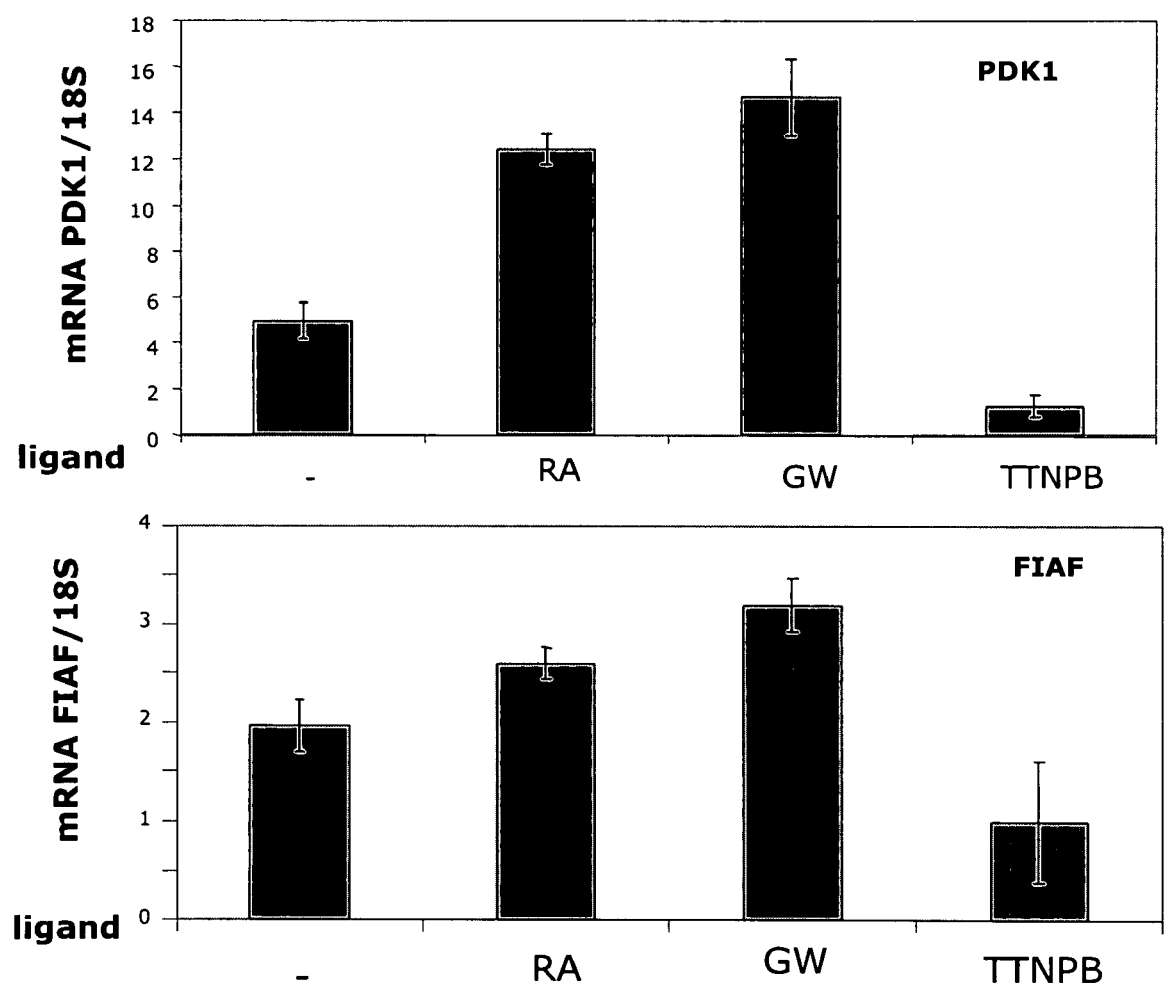
FIG. 4 illustrates a graph that shows retinoic acid activates PPAR β/δ in adipocytes.

The data in FIG. 4 shows that both FIAF and PDK1 are upregulated in these cells in response to the PPAR β/δ-ligand, attesting to the presence and functionality of this receptor in adipocytes. The data also show that, while activation of RAR by TTNPB resulted in down-regulation of the two genes, retinoic acid mimicked the PPAR β/δ-ligand and enhanced the expression of these genes.

Hence, retinoic acid activates PPAR β/δ in adipocytes, thereby inducing the expression of PDK1, a protein that plays central roles in mediating the cell responsiveness to insulin.

These observations suggest that retinoic acid will significantly sensitize cells to insulin actions such as the hallmark of insulin activity: enabling glucose uptake.

Example 3

We have now completed a pilot experiment to examine the notion that all-trans-retinoic acid (RA) suppresses obesity and insulin resistance. Experiments were carried out using both cultured adipocytes and a diet-induced mouse model of obesity.

For the in vivo experiments, C57BU6J mice were fed a high fat/high sucrose diet for 16 weeks, when they weighed 1.5 fold more than a cohort fed a standard diet. The obesity of these mice resulted in insulin resistance, the underlying cause for the development of diabetes. Obese mice were separated into two groups. Both groups were continually maintained on the high fat/high sucrose diet, and one of them was systemically treated with RA.

Figure 5:
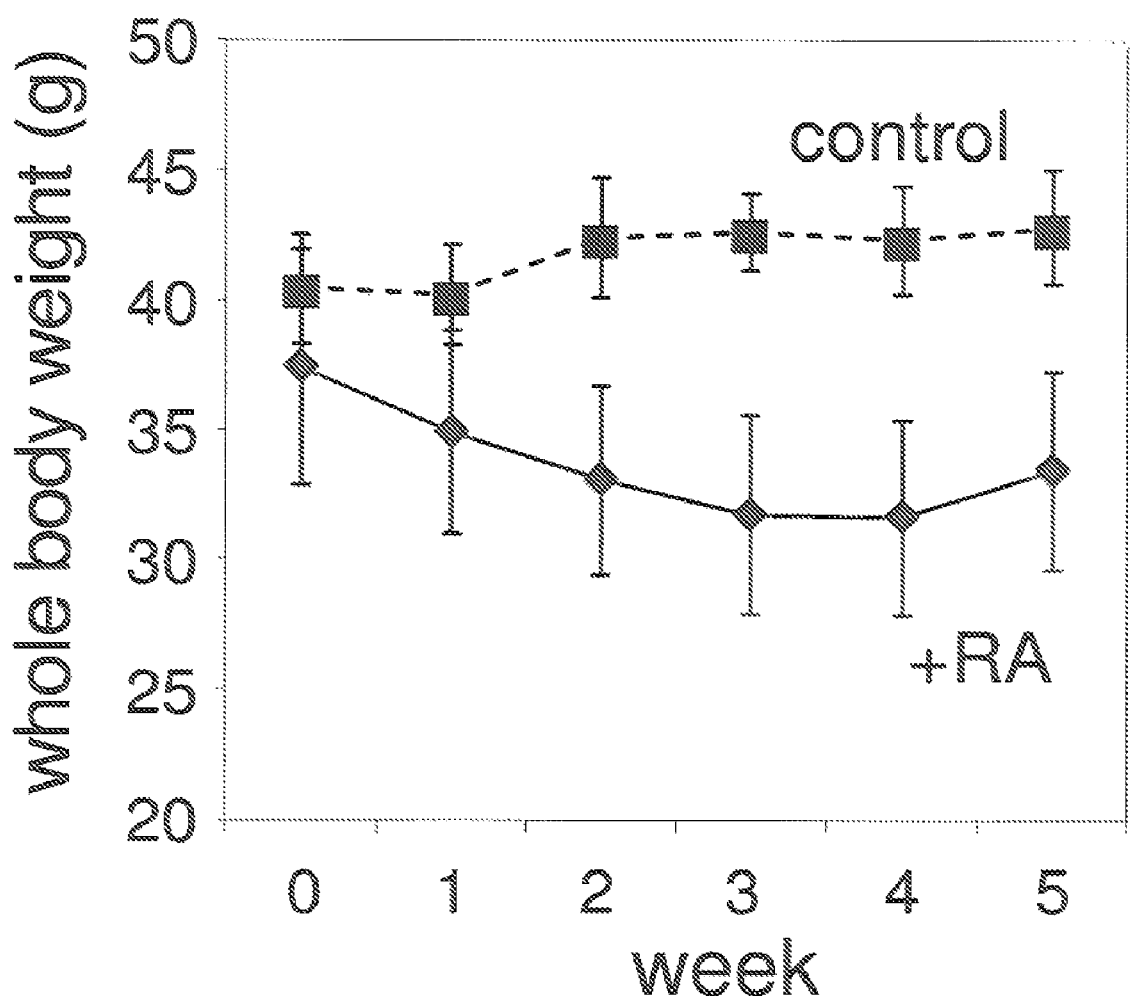
FIG. 5 illustrates Whole body weight of mice fed a high fat/high calorie diet in the absence and presence of systemic treatment with RA (0.16 mg/day).

A five week RA treatment led to a loss of ~15% body weight (FIG. 5)

Figure 6:
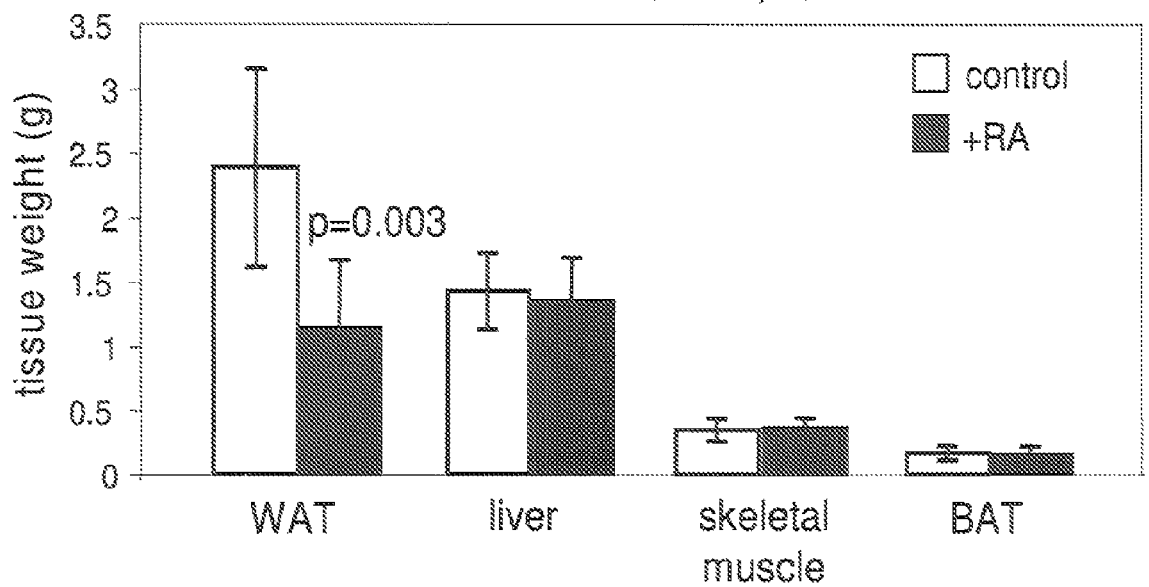
FIG. 6 illustrates RA treatment reduces the mass of white adipose tissue (WAT) without affecting the weights of liver, skeletal muscle or brown adipose tissue (BAT).

Weight loss in the mice stemmed almost exclusively from reduced weight of fat tissue, which decreased by over two fold (FIG. 6).

Figure 7:
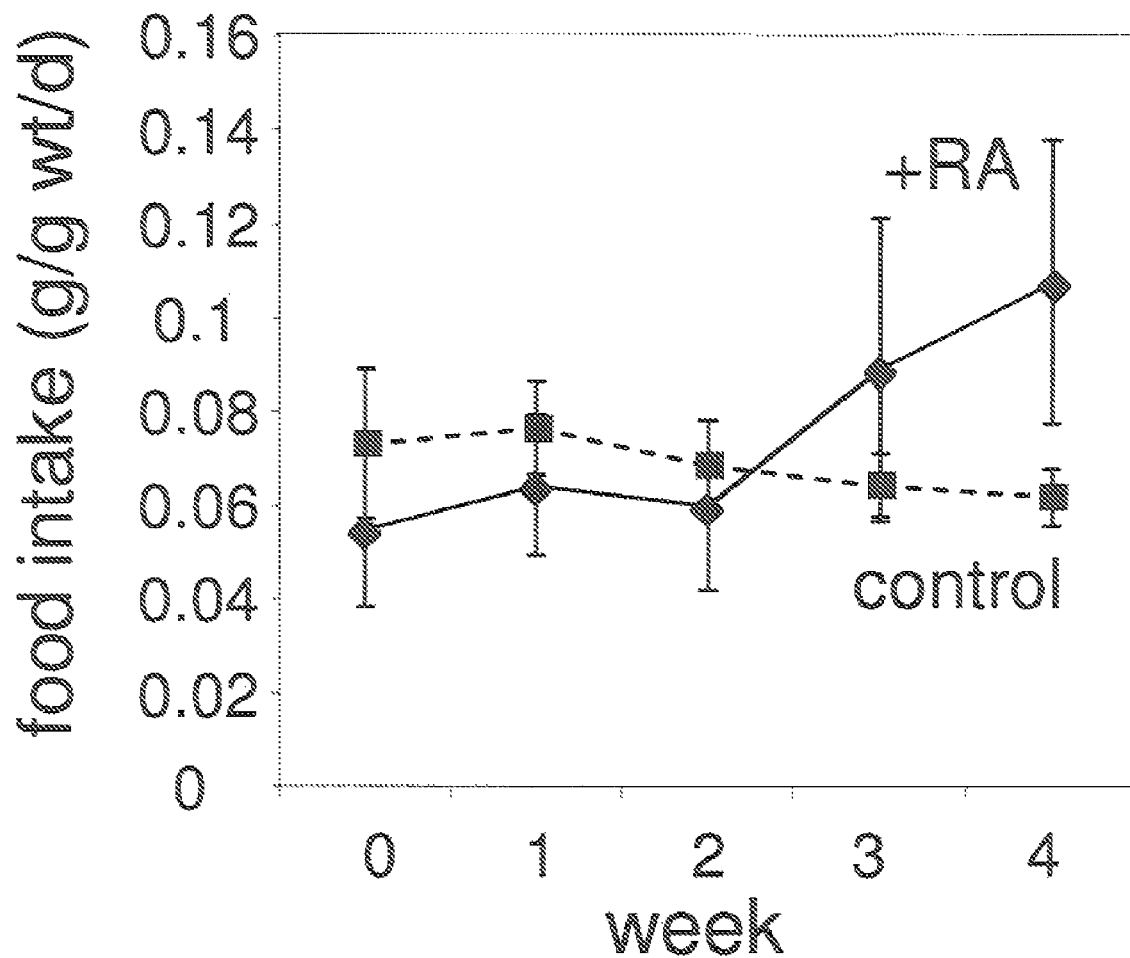
FIG. 7 illustrates RA treatment increases the food consumption of mice maintained on a high fat diet.

Remarkably, the food consumption of RA-treated mice was higher than that of the non-treated cohort (FIG. 7). Hence, the reduced adiposity stemmed from enhanced energy utilization rather than lower intake.

Figure 8:
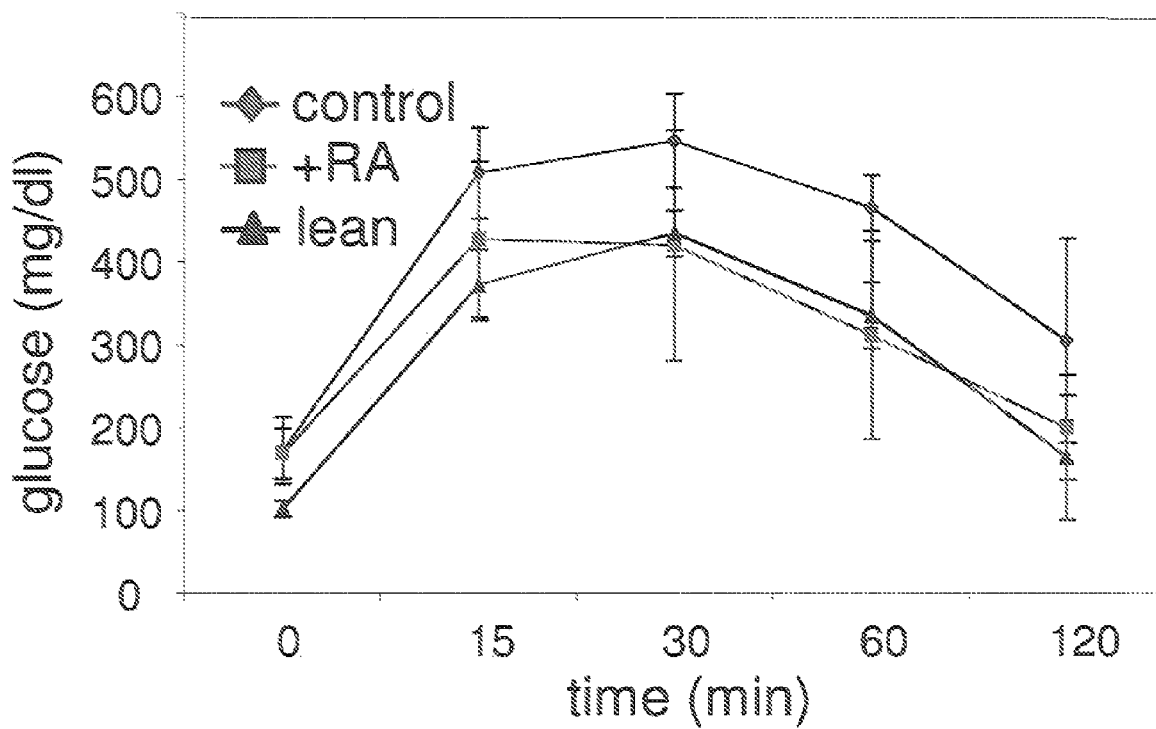
FIG. 8 illustrates RA treatment restores the ability of mice fed a high fat diet to rapidly clear glucose from blood. Control—obese mice fed with a high fat diet; +RA—mice fed with a high fat diet and treated with RA; lean—mice fed a standard diet.

An important measure of insulin sensitivity is the ability of an animal to clear glucose from plasma. This parameter is assessed by glucose tolerance tests (GTT) in which glucose is administered to the mice and the kinetics of its clearance from blood measured. As shown in FIG. 8, obese mice displayed a significantly more sluggish response in a standard GTT test as compared with lean mice. Strikingly, RA treatment improved glucose tolerance tests to an extent that their response was similar to that of lean mice.

Figure 9:
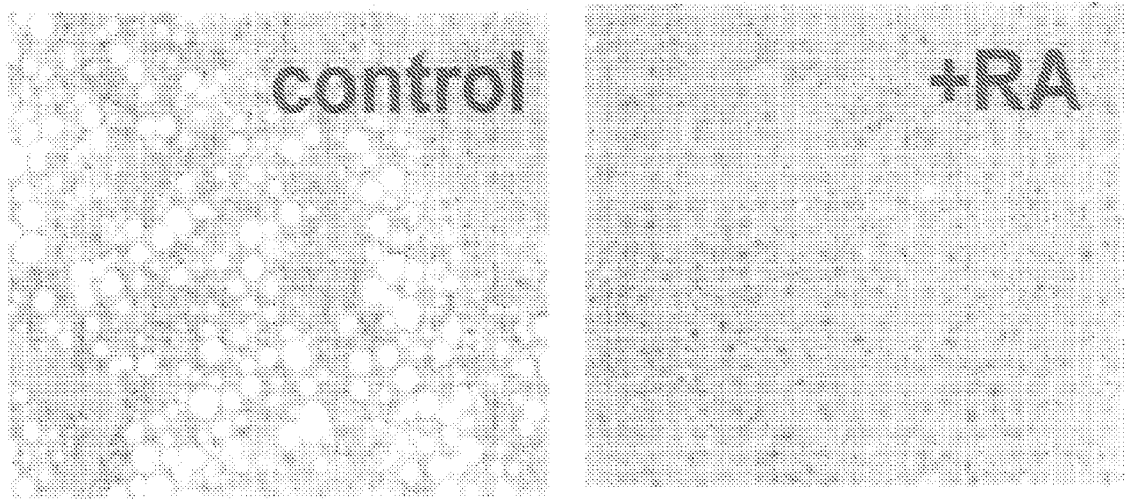
FIG. 9 illustrates livers of obese mice display pronounced steaosis and RA treatment reverses this detrimental phenotype.

One detrimental consequence of insulin resistance is the development hepatic steatosis, i.e., accumulation of lipids in liver. As shown in FIG. 9, livers of obese mice displayed a high level of hepatic lipid accumulation. In contrast, livers of mice fed a high fat diet and treated with RA were all but devoid of lipid stores.

CONCLUSIONS

In vivo, RA markedly suppresses adiposity and protects against insulin resistance even in the face of a high intake of a high fat/high calorie food.

From the above description of the invention, those skilled in the art will perceive improvements, changes and modifications. For example, it should be appreciated that the expression of FABP5 may upregulated in cells by, for example gene therapy, to increase insulin sensitivity and/or survival of the cells either alone or in conjunction with the administration of the all-trans-retinoic acid. Additionally, it will be appreciated that the all-trans-retinoic can be administered with other agents, such insulin and other insulin sensitizers to treat metabolic disorders. Such improvements, changes and modifications within the skill of the art are intended to be covered by the appended claims.

Having described the invention, the following is claimed:

1. A method of increasing the insulin sensitivity of insulin resistant cells in a subject with metabolic syndrome, administering to the cells an amount of all-trans-retinoic acid effective to activate transcription factor perosixome proliferator-activated receptor (PPAR) β/δ of the cells.

2. The method of claim 1, the all-trans-retinoic acid being administered at amount effective to induce expression in the cells of at least one of 3-phosphoinositide-dependent protein kinase 1 (PDK-1), fasting induced adipose factor (FIAF) or adipose differentiation-related protein (ADRP).

3. The method of claim 1, the insulin resistant cells comprising insulin resistant adipocytes.

4. A method of treating metabolic syndrome caused by insulin resistance of cells in the subject, comprising:
   administering to the subject an amount of all-trans-retinoic acid effective to increase the insulin sensitivity of the insulin resistant cells and treat the metabolic syndrome.

* * * * *